United States Patent [19]

Snider

[11] Patent Number: 4,560,555

[45] Date of Patent: Dec. 24, 1985

[54] REACTIVE POLYMERS FOR DERMAL AND TRANSDERMAL THERAPY

[75] Inventor: Bruno Snider, Capiago Intimiano, Italy

[73] Assignee: Sogimi s.r.l., Fino Mornasco, Italy

[21] Appl. No.: 560,867

[22] Filed: Dec. 12, 1983

[30] Foreign Application Priority Data

Dec. 17, 1982 [IT] Italy ................................ 24839 A/82

[51] Int. Cl.$^4$ ............................................. A61K 31/74
[52] U.S. Cl. ...................................................... 424/78
[58] Field of Search .......................................... 424/78

[56] References Cited

U.S. PATENT DOCUMENTS 4,250,267 2/1981 Hartdegen et al. ................. 435/317

Primary Examiner—Leonard Schenkman
Attorney, Agent, or Firm—Browdy and Neimark

[57] ABSTRACT

Reactive polymer coatings for the treatment of skin disorders, constituted of cross-linkable polyurethanes, that have film properties, and are suitable to be applied to the skin in need of treatment are generally constituted of two components to be mixed at the usemoment, so that the cross-linkage mostly happens through interaction with the proteic components of the treated skinparts. These formulations are also good carriers for transdermal action drugs.

7 Claims, No Drawings

REACTIVE POLYMERS FOR DERMAL AND TRANSDERMAL THERAPY

FIELD OF THE INVENTION

This invention regards reactive polymers for the treatment of skin afflictions and particularly crosslinkable urethane polymers with film properties and applicable to various skin disorders, and also to healthy skin as transdermal drugs supports.

BACKGROUND OF THE INVENTION

It is known that various treatments of skin diseases or the like has been proposed and used over the years, mostly through topical application of liniments, unguents or caustic agents such as nitric acid, chloracetic acid, salicylic acid, etc.

Moreover, for many years, the use of natural or synthetic polymers that have a relative affinity with skin tissues, have been employed as protective agents or as excipients and carriers for dermoreactive substances.

Prior products of external medical action, to be classified in the cathegory of liquid plasters for "spray" application, supply protection films, owing to evaporation of the solvent constituted to water or of water mixed with organic compatible solvents. Other similar products are mixed compositions of polymers and medicinal additives (emostatics, disinfectants, antibiotics; dermoprotectives). These prior products consist mostly of copolymers whose duration "in situ" after application, is of very few days, because of their sensitivity to water and perspiration. Their use is anyway suggested for the medication of wounds of small or medium dimensions, and the principal advantage of these materials is often limited to their easy use. Compounds belonging to this family have been also obtained with natural polymers of cellulosic kind, more or less chemically modified. Anyway, they are always products having a certain water sensitivity, that adhere to skin only through physical bonds.

In the literature of the field, it was mentioned also the use in exceptional cases of chemical unsaturated reactive substances, that, applied on serious wounds, with hemorrage danger, facilitate the arrest of the blood flow of wounds, due to a violent hemostatic action. These chemical substances are monomers of the cyanoacrylate family, that at skin contact, and by means of its humidity, polymerize, in that they are hydro-reactive products and chemically combined in correspondence to wounds.

Anyway, these products are not suitable for the normal epidermal and transdermal skin therapy, because of the absolute lack of elasticity and because of chemical toxicity, negative aspects that could be only accepted in drastic situations (serious wounds in war situations, mutilations, dangers of serious hemorrages).

Filmogenic polymers, endowed with hydrorepellent action, used in order to isolate recent wounds or sores, sensible to the soaking water effect, are recent introduction in the pharmaceutical field. Similar to the above mentioned polymers are for example alkylpolysiloxanes and other siliconic basis polymers that deposit upon skin through physical adhesion. They were used in the treatment of bedsores.

Of more recent vintage is the use of a polymer on the basis of animal collagen fibres, used alone or in combination in separate layers, with siliconic polymers, which always constitute the external protective layers.

SUMMARY OF THE INVENTION

It has been surprisingly discovered, and this is the object of the present invention, that certain urethane polymers, besides having superior mechanical and chemical characteristics, than the polymers known until now for analogous employments, present the properties of chemically binding to skin proteins, and more generally to bodily ones, showing a real therapeutical action on the alterations of animal skin, particularly human one. According to the present invention, the principal characteristics of polyurethanes are: dermoreactivity, that is the capacity of closely binding to skin through chemical reaction; elasticity very similar to that of skin; a good resistance to abrasion as well as a good resistance and impermeability to water.

These polymers, applied to skin as thin film, completely react with and remain bound to skin until the exchange of the horny layer and they protect the underlying derma in the reconstructive phase and accelerate the regeneration through stimulation of the damaged tissues. So, the resultant polymeric film has elasticity characteristics similar to those of skin, following contours and deformations, superior mechanical characteristics, good resistance to the soaking action of water and to the attack of substances of ordinary occasional use that can cause skin troubles, particularly if sensitive, such as detersives, certain cosmetics and others. It is usually waterproof having partial air-permeability but it is possible to modify the formulation to allow a greater ratio of air penetration, and consequently to improve the oxygenation of the deepest skin layers.

DESCRIPTION OF THE PREFERRED EMBODIMENT

According to the present invention, dermoreactive polymers are constituted to two components that are combined by mixing them immediately before the application on to the skin surface to be treated, and by leaving the applied coating to react for a determined period of time specifically for the application in question. The resultant polymers have a very high molecular weight and are cross-linked with a three dimensional structure, being very resisting even to the most common organic solvents; they steadily adhere to the epidermis and remain thereon for a variable period of time, that ranges from few days to three weeks about, that is until the healthy skin layers entirely regenerate. Just then, during the separation of the horny layer, owing to regeneration, the polymer film is removed therewith, leaving the new and healthy skin surface.

The first component A is an oligomer, with hydroxylic, amidic or aminic chemical functions. The second component B is constituted of a monomer, mostly an oligomer with isocyanate reactive chemical functions. The resultant reaction principally reguards hydroxylic, aminic or amidic and isocyanate groups according to the schematic equations well-known in the chemistry.

Another kind of reaction is the one that happens between the isocyanate groups and water, present in the atmosphere leaving the skin damp or in the skin exudate, with formation of new aminic groups, and the liberation of carbon dioxide, helping in this way the cross linkable reactions.

The —NCO functions of isocyanates react even with aminic and amidic hydrogens of the polypeptidic chains constituting the skin organic tissues according to the following schematic equation:

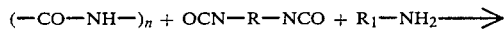
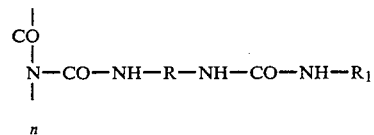

This reaction has a fundamental importance, from the point of view of the present invention, because it determines the polymer adhesion to skin. The polymer's reaction with damaged epidermic layers or anyway with superficial tissues determines a gradual devitalization of unhealthy skin cells, so to facilitate the body's rejection mechanism and to stimulate the regeneration of healthy cells.

In order to effect exactly the polymer's application, according tot he present invention, it's necessary that the part to be treated is clean as possible from fatty substances and dry, so to facilitate the perfect adhesion and the sealing surface action of the polymer film. For this reason, in the cases of pathologies with the presence of damp surfaces, it's necessary to dry the skin with absorbent materials having a large absorption capacity. For the most difficult cases in this sense, it will be useful to employ a combination of components at rapid reaction, so that the polymer in formation quickly binds to the surface and so it acts as barrier and stops the humor flow.

The pathologic cases in which the product, according to the present invention, has given the most evident results, are the different kinds of eczema or of dermatitis of allergic-toxinic origin, funginic, bacteric or chemical origin; troubles such as rhagades, chilblains, bedsores, burn sores and burns in general.

Most cases, examined in practical experiments, regard afflictions of chronic character, where therapy of modern medicine and pharmacology did not succeed in curing the disease: these were cases where one had often to deal with cortisone treatments, in order to mitigate temporarily the disease inconvenience, but that as it's known, reduces the efficacy of the immunity system, and anyway does not succeed in healing. The application of this kind of polymer, instead, could provide an effective treatment.

In the choice of substances, used for therapeutic formulations, according to the present invention, it is preferred to use, if possible, natural products; anyway, in order to get more sophisticated characteristics to the finished product, substances of synthesis were also taken into consideration.

So, a classic formulation is on castor oil basis, chemically constituted, mostly by tryglycerid of castor fatty acid, that reacts through its hydroxylic groups with isocyanates of isocyanate polymer.

Also in this case as in the most considered ones, the formulation is constituted to two components to be mixed at the use moment, parts A having hydroxilic aminic or amidic functions, and B having isocyanate functions.

Component A can be formulated with synthesis products, obtained through reaction of polyvalent alcohols with mono or polycarboxylic acid, preferably of aliphatic or cycloaliphatic series. The product, synthesized through polycondensation, has a molecular weight preferably between 500 and 2000 and a medium-low viscosity, in order to allow a lowest use of organic solvents. This component A can also be obtained from natural oil, prereacted, with polyvalent alcohols with consequent formation of hydroxylated glycerid successively reacted with carboxylic acids. Natural ooils, mostly taken into consideration for such aim, are the following: linseed, castor, soya, grape-stone, maize, safflower, sunflower, groundnut, fish, oiticia, tung, perilla, cotton-seeds, olive, almond, nut, hazel, coco-nut, palm oils, and other ones of vegetal or animal derivation, to be included into the chemical family of tryglycerids of fatty saturated and unsaturated acids.

As polyvalent alchols, there can be used glycols such as ethylenic, propylenic etc. and their polyoxyalkylenic derived polyalcohols such as glycerin, trimethylolpropane, penthaeritrithol, exanetriol, sorbitane, exoses, saccharose. Monovalent alcohols can be also used as modifying agents.

Monocarboxylic synthetic aliphatics or of natural origin can be used as carboxyilic acids such as fatty acid, bi- and polycarboxyilic ones, as succinic, adipic etc, phthalic, isophthalic, terephthalic, tetrahydrophthalic, exahydrophthalic, endomethylente-trahydrophthalic, hydroxyacids, aminoacids, or lattons can be also included into the formulation of component A.

Component A can be also constituted of a copolymer urethane hydroxylated, obtained through reaction of a polyvalent alcohol, eventually modified for esterification or copolymerization with a polyisocyanate.

Component A can be also a copolymer obtained from unsaturated monomers having OH alcoholic or OH phenolic groups, amidic or aminic such as residue functions.

Analogously, component A can be also a polyamide or polyesteramide, at preferably low molecular weight or a polyether obtained through condensation of polyvalent alcohol with alkylenics or with chloridrine or a polyamine with aminic secondary hydrogens, preferably sterically hindered.

Component A can be also constituted of lattons polymers.

As regards the formulation of components B, it's principally characterized by the presence of isocyanate radicals (—NCO). Among substances that have these requirements, are included isocyanates or oligomers, obtained through addition of polyalcohol with isocyanates such as isophorondiisocyanate, trimethylexamethylendiisocyanate, examethylendiisocyanae, dicycloexylmetandiisocyanate. Though less suitable, other substances of this kind, are addition products or aromathic isocyanate based oligomers such as toluendiisocyanate, diphenylmethandiisocyanate. As component B, there can be used allophanate trimers of aliphatic isocyanates or cycloaliphatic, above mentioned, and also isocyanurate trimers thereof, and allophanate or isocyanurate copolymers of isocyanates, or even mixtures of pure trimers of copolymers between themselves.

Since the essential characteristic for the determining of therapeutic properties of products, according to the present invention, is the presence of isocyanates groups, to which is attributed the capacity of chemically binding with skin proteins, component B can be also the unique component on condition that it has physical-mechanical characteristics, suitable to the task of skin-protection. Anyway, the formulation of the product with two components to be mixed at the application moment, offers more possibilities in modifying characteristics because it allows the addition of solvents as regulators of viscosity, of matting agents, dyes, permeability agents, auxiliary drugs at percutaneous action in A, that chemically is the stablest part.

Additives that belong to the formulation of component A, are really important because they help to improve the product performances. So, in order to fit the film opacity to the natural one of skin, and to satisfy aesthetic requirements, there can be used natural or synthetic waxes, microdisposed in opportune solvents or in microdust state; paraffins at selected melting point; dust organic matting agents such as polyethylene, polypropylene, polytetrafluorethylene or similar copolymers of silicic nature, or on carbonates basis, preferably of cacium and magnesium or aluminum hydroxide and oxide basis.

Solvents eventually used, are chosen among those that present the best chemical-physical compatibility for skin, and a volatility as high as possible, so as to remain as short a time as possible in contact with the treated part. Auxiliary drugs that can be used, must be selected among theinert ones in comparison with the isocyanate groups, in order to avoid interaction, and they must be used in active form free from functions that interfere in the reaction witht he polymer. Specially when the polymer is used for transdermal absorption of drugs there are employed as carriers substances having solvent function as triacetine (glycerine triacetate), dimethylsulfoxide, butyl stearate, ethyl or methyl linoleate, methylpyrrolidone, ethylcaprylate, or other superior esters or solvents suitable for treatment. As aeropermeability agents of applied film, there can be considered hydrophilic fibrous fillers or simplier idrosoluble polymers dissolved in organic solvent not reactive with isocyanates.

EXAMPLE 2

523 parts of decanediol, 404 parts of sebacic acid, and 0.4 parts of tin dibutildilaurate are reacted under the conditions of Example 1, until there is obtained a polyester having an acidity index=0.5 and hydroxilic number=135.

EXAMPLE 3

536 parts of polyethoxylated glycerin (molecular weight=268), 116 parts of fumaric acid, 138 parts of salicylic acid, and 1.5 parts of tin dibutyldilaurate are reacted under conditions of Example 1, to obtain a polyester having condensation point=99.9%.

EXAMPLE 4

890 parts of soya-bean oil, 140 parts of penthaeritrytol and 0.3 parts of stannous chloride are reacted at 325° C. with the formation of a monoglyceride. The obtained monoglyceride is reacted with 146 parts of adipic acid at 200° until a polyester is obtained having an acidity index=1 and hydroxilic number=98.

EXAMPLE 5

Example 4, is respeated with the difference that soya-bean oil is replaced witht he same quantity of dehydrated castor oil. A polyester having analogous characteristics is obtained.

EXAMPLE 6

900 parts of fish-oil (sardine oil) with 184 parts of glycerin and 1 part of tin dibutyldilaurate are reacted at 235° in order to obtain the oil monoglyceride. this is cooled at 50° and reacted with 420 parts of trimethyl-hexamethylenediisocyanate, until there is obtained a product having an isocyanic number=0, and hydroxylic number=75.

EXAMPLE 7

174 parts of 1,10 decanediol, 938 parts of castor oil and 222 parts of isophorondiisocyanate are reacted as in Example 6 to obtain a polymer having isocyanic number=0 and hydroxylic number=114.

EXAMPLE 8

158 parts of trimethylhexamethylenediamine, 280 parts of oleic acid and 300 parts of hydrossistearic acid are reacted at 200° C. so to obtain a polyamide having acidity index=1, hydroxylic number=80 and equivalent hydrogenamidic 350.

EXAMPLE 9

There are reacted 134 parts of trymethylolpropane and 1068 parts of propylene oxide in the presence of 0.03 parts of metallic sodium at 5 Atm pressure, and 140° C. temperature until there is obtained a polyester having an hydroxyl index 140. At the end of reaction, the polyether is neutralized with 0.3 parts of magnesium hydrogenphosphate, MG Mg(H$_2$PO$_4$)$_2$ and is filtered so to obtain a limpid product.

EXAMPLE 10

The following starting compounds are used to prepare a prepolymer A:

| | |
|---|---|
| CASTOR OIL | 938 |
| ADIPIC ACID | 438 |
| 1-10 DECANEDIOL | 174 |
| 1-6 HEXANEDIOL | 236 |
| | 1786 |

In a reaction vessel suitable for effecting esterification the Castor oil, Adipic acid, 1-10 Decanediol and 1-6 Hexanediol are charged keeping the atmosphere of the reactor under nitrogen stream. The mixture is esterified by heating, mixing the ingredients to the temperature of 200° C. under conditions of azeotropic recycle, using toluene as carrier solvent. In this way, the chemical-reaction-water is extracted and separated continuously from toluene in a suitable phase separator. In the rectification column, the temperature of the vapors at head of column are controlled so as not to exceed 100°. The vapors of reactions are condensed in a water-cooled condenser. The reaction is continued until the complete extraction of the theoretical reaction water (108 g) and until the acidity value of the prepolymer is equal or less than 0.5 and the hydroxyl number equal to 92.

The product is distilled under vacuum of 10 TORR the toluene and cooled to 50° C. The produce so obtained can be better transformed in component A by adding catalysts like tin dibutyldilaurate (0.05–1 percent) alone or together with tertiary aliphatic amine as triethylamine (0.05–0.5 percent) and solvent like acetone in order to give at the final product a reacxtivity degree and flow more suitable to the specific application.

COMPONENT B

EXAMPLE 11

510 parts of 1,6 hexamethylenediisocyanate are reacted with 18 parts of water in conditions known per se, in order to obtain at the end of reaction a biuret structured polymer with a NCO content equal to 24% of an hexamethylenediisocyanate monomeric content less than 0.2%.

EXAMPLE 12

168 parts of 1,6 hexamethylenediisocyanate, 222 parts of isophorondiisocyanate, 210 parts of trimethylhexamethylenediisocyanate and 18 parts of water are reacted in conditions known per se, in order to obtain at the end of reaction a biuret structured polymer with a content at NCO functions equal to 20% and a content of monomeric diisocyanate less than 0.3%.

EXAMPLE 13

440 parts of isophorondiisocyanate and 210 parts of trimethylhexamethylenediisocyanate are reacted at the presence of 0.2 parts of sodium methylate under conditions known per se, in order to obtain an isocyanurate monomer, having a NCO content equal to 16.8 and a diisocyanate monomeric content less than 0.3%. The obtained polymer is diluted with anydrous ethyl acetate and the sodium ion is eliminated with 1.2 parts of ortho-cholorobensoyl chloride, and filtering on ultraanydrous paper.

EXAMPLE 14

Through addition reaction of 174 parts of 1,10 decanediol with 420 parts of trimethylhexamethylenediisocyanate in conditions known per se, there is obtained a product having a content of —NCO functions equal to 13.8% and free isocyanate monomeric content less than 0.3%.

EXAMPLE 15

212 parts of myristylamine are reacted using conditions known per se with 420 parts of trimethylhexamethylenediisocyanate and at the end of reaction, there is obtained a product having a percentage of —NCO functions equal to 12.6% and a free monomeric isocyanate less than 3.0%.

EXAMPLE 16

By reacting 420 parts of trimethylehexamethylenediisocyanate and 228 parts of diisobutylhexamethylenediamine under conditions known per se, at the end of reaction there is obtained a product having a percentage of —NCO functions equal to 12.3% and content of free monomeric isocyanate less than 0.2%.

The product obtained has been employed in the treatment of skin effections according to the present invention.

EXAMPLE 17

The following starting substances are used to prepare a prepolymer B:

| | |
|---|---|
| TRIMETHYLHEXAMETHYLENEDIISOCYANATE | 210 parts/wt |
| HEXAMETHYLENEDIISOCYANATE | 336 |
| 1-10 DECANEDIOL | 130 |
| DISTILLED WATER | 9 |
| ETHYLENEGLYCOL-DIMETHYLETHER | 670 |
| ACETONE | 75 |
| | 1430 |

In the reaction vessel are charged trimethyl-hexamethylenediisocyanate and hexamethylenediisocyanate. The reactor is purged with anydrous nitrogen and heated to the temperature of 80° C.

There is prepared a solution mixing 1-10 decanediol-water-ethyleneglycol dimethylether and the above solution is added gradually in 8 hours keeping the temperature in the reactor at 80° C.

Solvent vapours of ethyleneglycol-dimethylether are condensed in a water cooled condenser and recycled in the reactor.

After completion of the addition of solution, the product is kept in the reactor always at 80° C. It is distilled by heating gradually at 100° C. recovering the solvent.

A vacuum at 10 Torr is applied to the reactor by keeping the temperature at 100° C., including between the reactor and the vacuum pump an extra condenser and recovery tank are precooled at −35° C. These conditions of vacuum are kept for 30 minutes. The vacuum is stopped and the atmosphere in the reactor is saturated with nitrogen.

The propolymer above obtained is treated in a thin-layer-evaporator continuously under vacuum of 0.1 TORR and with evaporator wall's temperature of 125° C. This treatment is done to reduce at the minimum value the content of free diisocyanate monomer. The prepolymer is cooled at 40° C. and diluted with anydrous acetone.

The final product contains reactive NCO groups in a percentage of 15.4% and a content of free diisocyanate monomers of 0.3%.

COMBINATIONS OF COMPONENT A+B

EXAMPLE 18

To 90 parts of polyester, obtained according to Example 1, are added 9.8 parts of ethylacetate, 0.1 parts of paraffin having melting point at 90° C., and 0.1 parts of tin octoate, in order to obtain a finished product corresponding to component A, according to the present invention. This component A is mixed at the moment of use with the biuret polymer obtained in Example 11 in a careful ratio included between 3:1 and 5:1 for the treatment of skin affections.

EXAMPLE 19

99 parts of the polymer obtained according to Example 9 and 1 part of tin dibutyldilaurate are combined at the application moment with the isocyanurate polymer obtained in Example 13 in a careful ratio varying between 1:1 and 3:1.

Formulations so obtained have been used in the treatment chronical eczema, lasting for 2–5 years and judged incurable because the cures, executed before on the basis of linaments and compounds, according to the modern pharmacology, did not give any tangible result, while cortisone medicines desultorily used, sometimes provided improvements, but the pathology successively appeared.

The application of the product, according to the example, provide the formulation of soft films, that keep themselves integral for a variable period of time, ranging from about 7 to 20 days, according to cases, showing large resistance to water and to wear and tear, particularly when applied to the hands. With the film separation, because of the renovation of the skin horny layer, good results were mostly obtained. In the few cases in which the result was not resolutive, a second treatment or eventually a third one, in the most difficult cases, determined the complete healing.

EXAMPLE 20

95.65 parts of anhydrocastor oil, 0.05 parts of tin dibutyldilaurate, 0.1 of paraffin at melting point 48° C., 2 parts of beta-carotlene, and 2 parts of powdered polyethylene having a maxima particle size of 50 micron, are combined at the application moment with a product obtained through trimerization of the trimethylhexamethylenediisocyanate (trimer allophanate), according to respective careful ratios included between 1:1 and 2.5:1 for the treatment of skin afflictions.

EXAMPLE 21

91 parts of the polymer obtained according to example 7, 10 parts of N-vinylpirrolydone, one part of benzoinethylether and 1 part of tin dibutyldilaurate are mixed at the application moment with the allophanate polymer, according to Example 11 in respective careful ratios included between 2:1 and 4:1 for the treatment of skin afflictions.

EXAMPLE 22

99 parts of the product obtained according to Example 6, 0.5 parts of cobaltous octoate, and 0.5 parts of calcium octoate, are combined at the application moment with the isocyanurate polymer according to example 12, preferably in the ratio of weight 2:1 respectively for the treatment of skin afflictions.

EXAMPLE 23

Combination of products according to Example 1 to 9 with products according to examples 10 to 15, are used for exzema cures, dermatitis, fungic afflictions, and bedsores with positive resolutive results, after 20 days from the starting of the treatment.

EXAMPLE 24

A combination of products, as pointed out at Example 18, was used in order to treat a mycosis form that manifested with whitish plaques on a patient's leg.

The combination was applied immediately after the A+B mixing, with a brush in order to cover completely the infested parts (about 150 cmq on the whole). After about 4–5 days the applied polymer film spontaneously peeled off, leaving a skin surface a little reddened. The polymers application was successively repeated and the resulting film polymer kept adhered to the skin for a much longer period of time and separated after about 15 days. At the end, the treated part was completely healed and there were no relapses.

EXAMPLE 25

A components combination according to what is described in Example 20, was applied to the left cheekbone temporal part of a patient afflicted with skin-alteration of unsure diagnosis (psoriasis or lupus). 20 minutes after the application the patient already felt a beneficent sensation of moderate warmth at the site of application which replaced the burning sensation.

After 40 minutes, the cross-linked film was dry, with perfect elasticity which did not give any unpleasant sensation of superficial stretching. In the meantime, spasms due to superficial nervous contractions that, before the treatment, determined local microwounds, disappeared. The separation of the polymer film happened after about 20 days. There resulted immediately the suspension of ache, and the diminution of The red livid colouring. A second application was made and after another 15 days the polymer layer separated. The surface undulying skin was rose-coloured, typical of skin in a healing phase. At the end, there was executed a third application, to which the reconstitutive phase of skin followed. The doctor judged that the reconstituted skin presented an aspect really better than the one regarding analogous cases of healings, obtained with radiotherapic treatments, combined with applications of specific medicines.

With reference to this, it is very important to note that the soothing action in comparison with inflammatory manifestations, due to reactive polymers according to the present invention, suggests anti-histaminic properties in the treatment of the infection. In fact the isocyanate radicals chemically block and neutralize the histamine molecules that free themselves from tissues in concomitance with unhealthy phenomena, and bind to the aminic groups belonging to them.

EXAMPLE 26

A case of skin pathology, in which the formation of superficial chaps appeared, more properly of rhagades on the palmar surface and between the fingers and on the plantar feet part, was with a combination of products according to Example 18, and the condition was alleviated in short time. Immediately after the compound application, the classic rhagades burning disappeared; hands were kept with fingers wide apart and feet were kept free from the contact with foreign bodies for 30 minutes, until the getting of a fair degree of dessication. After 3 days, through the transparent polymer film, it could be already observed the complete wounds cicatrization.

EXAMPLE 27

Some products combination, according to Example 16, 18, 19, 20 and 22, were used for the treatment of hands and feet chilblains, with very good results, shown by neutralization of skin irritation, consequent to the particular pathology. After 15–20 days, the treatment was finished with perfect healing.

EXAMPLE 28

A compound combination as reported in Example 22 was used for the cure of bedsores at the sacral bodily part of an old sick woman.

Previously, the woman had been treated with frequent applications of siliconic products without any positive result, but with progressive extension of the wounded part.

The product application, according to the present invention, was executed after having well dried the part; the patient immediately felt a great benefit, so that she was able to lean on the part with more facility without feeling great pain; since previous siliconic applications partially compromised the film adhesion, according to invention it was necessary to repeat the application 5 days later.

The bettering was considerable, but because of the compromising of the part due to the previous treatment, it was necessary to apply a third treatment with products of the present invention, executed 15 days after the separation of the second polymer film. At the end there was obtained the perfect healing of the wounded part.

EXAMPLE 29

There is prepared a type of component A by mixing 60 parts of prepared product (as shown at Example 7), 0.2 parts of paraffin (melting point 50° C.), 20 parts of glycerine triacetate, 8 parts of glycerine trinitrate, 1 part of tin butyldilauate, 0.2 parts of triethylamine, 10 parts of ethyl caprylate and 2.6 parts of pryrogenic silica. The product, obtained in such a way, was thixotropic.

4 parts of this component A were combined, by mixing, with 1 part of component B, prepared as shown in example 10. This particular combination was spread, till the reaching of a thickness of 100 micron and a surface of 30 cmq, on the back of a patient subjected to therapy for angina pectoris. This treatment showed an efficacy protracted for 4 days, that is for all the time the film remained attached to skin. Therefore, it was not necessary to repeat the application every day as is often required when transdermal ointment is used. Besides, there was the advantage due to the possibility of doing the cleaning without removing the reserves in situ of medicament.

EXAMPLE 30

There was prepared a type of component A with 80 parts of product (according with Example 7), 0.5 parts of tin dibutyldilaurate and 18.5 parts of allyl acetylsalicylate. This preparation A was combined with component B in the ratio 3:1 (as shown in example 10). This product was spread till the reaching of a thickness of 500 microns and a surface of 50 cmq on the internal part of the right thigh of a subject suffering from rheumatism. The film remained attached for 5 days. During this period of time, the application showed efficacy in considerably reducing the pain of articulations and eliminating the typical rheumatoid shivering sensations.

EXAMPLE 31

There was prepared a type of component A with 98 parts of monodehydrated castor-oil (that is with a ricynoleic radical transformed into a conjugated linoleic radical by eliminating one water molecule), 0.1 parts of tin dibutyldilaurate and 1.9 parts of dimethylsulfoxide.

This component A was combined with component B in the ratio 3:1 (as shown in example 10). The combination was applied on burns sores having a surface of about 250 cmq on a patient's abdomen. Before the application, there was removed necrotized tissues and the part to be treated was hydienically prepared in order that it showed a low exudation. The applied product kept oily consistence for about 1 hour. After about 2 hours, the part kept in contact with air was almost dried. After 3 hours, a barrier film formed protecting the treated part. 15 days later, the gradual detachment of film together with the devitalized tissue surface occured. The surface burnt was free from sores. A further application was made and, 10 days later, after complete polymer film detachment, the skin epitelial tissue of the treated part was perfectly constituted and healed.

Though the present invention has been shown on the basis of some realized examples, it is obvious that variations and/or modifications will be able to be brought both to description and examples without departing from the spirit and going out the protective ambit of invention itself.

I claim:

1. A method of treating the human or animal skin comprising forming in situ a polymer film chemically bound to said skin, said film being obtained by coating the skin with a dressing selected from liquid isocyanate prepolymers alone or mixed with prepolymers having free hydroxy, amino or amido groups, together with additives, adjuvants, solvents and transcutaneously acting drugs which are not adversely affected by said liquid isocyanate prepolymers and said prepolymers having free hydroxy, amino or amido groups.

2. A method of providing a protective covering on skin of a human or animal in need of said therapy, comprising;
   applying to said skin a film-forming polymer composition prepared by mixing immediately prior to application to the skin, a liquid oligomer having reactive hydroxyl, amide or amine groups, and a cross-linkable liquid oligomer having reactive isocyanate groups.

3. A method according to claim 2 characterized in that said isocyanate prepolymer has a content of free isocyanate (—NCO) groups preferably ranging from about 12% to about 24%.

4. A method according to claim 2 characterized in that said oligomer having free hydroxy, amino or amido groups is selected from the group consisting of polyesters, polyethers, polyamides hydroxylated polyurethanes, and amino resins.

5. A method according to claim 4 characterized in that said oligomer having free hydroxy, amino or amido groups has an acidity index from 0.5 to 1, a hydroxy number between about 75 and 140 and a molecular weight between 500 and 2000.

6. A method according to claim 2, characterized in that the weight ratio between said oligomer having free hydroxy, amino or amido groups and said isocyanate oligomer is from 1:1 and 5:1.

7. A method of treating internal body diseases by coating some skin areas with film-forming polymer compositions, characterized in that cross-linkable liquid isocyanate prepolymers having free isocyanate groups are mixed just before the application with prepolymers having free hydroxy, amino or amido groups and containing effective amounts of transcutaneously-acting systemic drugs which are inert with respect to and not adversely affected by said isocyanate groups, or by said prepolymers having free hydroxy, amino or amido groups.

* * * * *